United States Patent [19]

Kondo et al.

[11] Patent Number: 5,456,258
[45] Date of Patent: Oct. 10, 1995

[54] CATHETER TYPE ULTRASOUND PROBE

[75] Inventors: Mituo Kondo; Kenji Abe, both of Omiya; Susumu Hiki, Otawara, all of Japan

[73] Assignees: Fuji Photo Optical Co., Ltd., Omiya; Kabushiki Kaisha Toshiba, Kawasaki, both of Japan

[21] Appl. No.: 359,823

[22] Filed: Dec. 20, 1994

[30] Foreign Application Priority Data

Dec. 20, 1993 [JP] Japan .................... 5-344575

[51] Int. Cl.⁶ ...................................... A61B 8/12
[52] U.S. Cl. ............................................. 128/662.06
[58] Field of Search ................ 128/662.03, 662.06, 128/663.01, 660.08, 661.01

[56] References Cited

U.S. PATENT DOCUMENTS

| | | | |
|---|---|---|---|
| 5,191,890 | 3/1993 | Hileman | 128/662.06 |
| 5,299,578 | 4/1994 | Rotteveel et al. | 128/662.06 |
| 5,348,017 | 9/1994 | Thornton et al. | 128/662.06 |

*Primary Examiner*—George Manuel
*Attorney, Agent, or Firm*—Oblon, Spivak, McClelland, Maier & Neustadt

[57] ABSTRACT

A catheter type ultrasound probe having an ultrasound transducer mounted on a rigid fore end section at the tip end of a soft and flexible body section of a catheter member to be introduced into an intracavitary portion. The catheter member includes an articular joint section which is connected between the rigid fore end section and the flexible body section, the articular joint section having front and rear joint members pivotally connected with each other for angular flexing movements in directions forward and rearward of an active face (a signal transmission and reception surface) of the ultrasound transducer on the rigid fore end section of the catheter member. A biasing mechanism is mounted on the articular joint section to urge a front joint member constantly rearward of the active face of the ultrasound transducer into a bent position off the axis of the catheter member along with the rigid fore end section. A joint operating wire is connected to the front joint member to turn same back into a straight axial position against the biasing force of the biasing mechanism.

4 Claims, 4 Drawing Sheets

CATHETER TYPE ULTRASOUND PROBE

BACKGROUND OF THE INVENTION

1. Field of the Art

This invention relates to a catheter type ultrasound probe with an ultrasound observation means incorporated into a tip end section of a catheter member to be introduced into an intracavitary portion for examination or other purposes.

2. Prior Art

Ultrasound examination systems are generally arranged to transmit ultrasound pulses toward a target portion through an intracavitary wall by driving an ultrasound transducer while receiving and processing return echo signals to display tomographic ultrasound images on a monitor screen. In this regard, there have been known in the art the so-called catheter type ultrasound probes which have an ultrasound transducer at the tip end of a flexible catheter member to be introduced into an intracavitary portion of interest. Some of such catheter type ultrasound probes are tailored to secure a view field of ultrasound image by means of a B mode ultrasound scanning system adapted for a linear or convex scanning operation with an ultrasound transducer under either mechanical or electronic drive. For example, in case of electronic linear or convex scanning operations, it is the usual practice to use a catheter member which has a plural number of ultrasound transducer elements arrayed axially in a row on its rigid tip end portion, driving the ultrasound transducer elements sequentially under electronic control to produce an ultrasound image over a predetermined view field.

When a diseased portion is spotted by an ultrasound examination, there often arises a need for penetrating a puncture needle into the diseased portion for injection of medicine or contrast medium, for sampling tissues or for drainage. The puncture needles which serve for these purposes generally has a hollow needle body with a sharp pointed end for penetration to an aimed depth of an intracorporeal portion. Such a puncturing operation is monitored through ultrasound images on a monitor screen to guide the needle point to a diseased portion or other locality which needs a treatment. The puncture needle of this sort is formed of a rigid pipe at least in its fore end portion to ensure smooth penetration into target intracorporeal portions.

In this connection, in case the ultrasound transducer consists of a plural number of transducer elements which are arrayed axially on a catheter member as mentioned hereinbefore, the catheter member necessarily needs to have a rigid fore end section which is axially elongated to support the transducer elements thereon. A problem with such a catheter member is the difficulty which is invariably encountered in passing the lengthy rigid fore end section through an angularly bent portion in an intracavitary path of insertion of the catheter member, for example, in inserting same into the esophagus around the angularly bent throat portion. Difficulties are also encountered in turning the rigid fore end section toward a particular direction within an intracavitary portion or in turning the active face of the ultrasound transducer closely toward a particular target portion of ultrasound examination. Further, for the purpose of monitoring the puncturing operation by way of ultrasound images under observation, it is necessary to launch the puncture needle from a position close to the ultrasound transducer and at a predetermined angle with the face of the ultrasound transducer, for example, at an angle of 30°, so that the needle point of a rigid pipe should fall within the view field of the ultrasound image under observation. This gives rise to another problem that it is extremely difficult to launch a rigid pipe puncture needle at such a large angle through a needle guide passage which runs axially through the catheter member and turns its direction acutely toward a needle exit opened on a lateral side of the rigid fore end section of the catheter member closely on the near side of the ultrasound transducer.

SUMMARY OF THE INVENTION

With foregoing situations in view, it is an object of the present invention to provide a catheter type ultrasound probe with a needle guide passage for a puncture needle on a catheter member to be introduced into an intracavitary portion for examination or other purposes, the ultrasound probe having means for ensuring smooth insertion of the catheter member through a bend in an intracavitary path of insertion even if it has a relatively lengthy rigid section at its fore end, while facilitating to face the ultrasound transducer on the rigid fore end section properly and exactly toward a particular intracavitary portion of interest and facilitating passage of a puncture needle through a needle guide passage turning toward a needle exit opening on a lateral side of the rigid fore end section.

In accordance with the present invention, the above-stated objective is achieved by the provision of a catheter type ultrasound probe having an ultrasound transducer mounted on a rigid fore end section at the tip end of a soft and flexible body section of a catheter member to be introduced into an intracavitary portion, characterized in that the catheter member includes an articular joint section connected between the rigid fore end section and the flexible body section, the articular joint section having front and rear joint members pivotally connected with each other for angular flexing movements in directions forward and rearward of an active face (a signal transmission and reception surface) of the ultrasound transducer on the rigid fore end section of the catheter member, a biasing means mounted on the articular joint section and constantly urging the front joint member rearward into a bent position off the axis of the catheter member along with the rigid fore end section, and a joint operating wire means connected to the joint member to turn same back into a straight axial position against the biasing action of the biasing means.

Normally, the rigid fore end section is retained in a bent position by the biasing means at a predetermined angle with the longitudinal axis of the catheter member. Accordingly, for example, on insertion into an intracavitary path which contains a bend of a relatively acute angle as at the throat, the passage of the rigid fore end section of the catheter member can be made easier by orienting the bent rigid fore end section to lie in the same direction as the bend in the path of insertion. In a straight path of insertion, the wire means is pulled to turn the rigid fore end section into the straight position axially in line with the remainder of the catheter member for smooth passage free of possibilities of being hooked on an obstacle portion which might exist in the path of insertion.

As soon as the rigid fore end section at the tip end of the catheter member has been introduced to a locality of intracorporeal examination, the ultrasound transducer on the rigid fore end section is held in intimate contact with an intracavitary wall portion of interest, or faced properly toward an intracavitary wall portion of interest through a balloon which is inflated and filled with an ultrasound transmissive medium in intimate contact with the intracavitary wall portion. No matter whether the ultrasound transducer is directly pressed into intimate contact with an intracavitary wall or faced toward an intracavitary wall through a balloon, it has to be disposed substantially in parallel relation with the intracavitary wall during an ultrasound examination. In this regard, the active face (the signal transmission and reception surface) of the ultrasound transducer on the rigid fore end section can be turned through a predetermined angle relative to the axis of the catheter member, so that the ultrasound transducer can be adjusted into an optimum direction or angle relative to a particular intracavitary wall portion by operating the above-mentioned wire means.

Further, the puncture needle guide passage which extends through the flexible section and through the rigid fore end section of the catheter member is terminated with an exit opening, which is opened on the girder of the rigid fore end section on the near side of the ultrasound transducer to launch a puncture needle into the view field of the ultrasound transducer. The needle guide passage which runs axially through the flexible section of the catheter member is turned toward the exit opening through a curved needle passage of a predetermined turn angle. As will be described in detail hereinlater, for the purpose of facilitating passage of a rigid puncture needle, the just-mentioned turn angle of the needle guide passage can be moderated by bending the rigid fore end portion in a direction rearward of the active surface of the ultrasound transducer.

The above and other objects, features and advantages of the invention will become apparent from the following particular description, taken in conjunction with the accompanying drawings which show by way of example a preferred embodiment of the invention.

DESCRIPTION OF PREFERRED EMBODIMENTS

Figure 1:
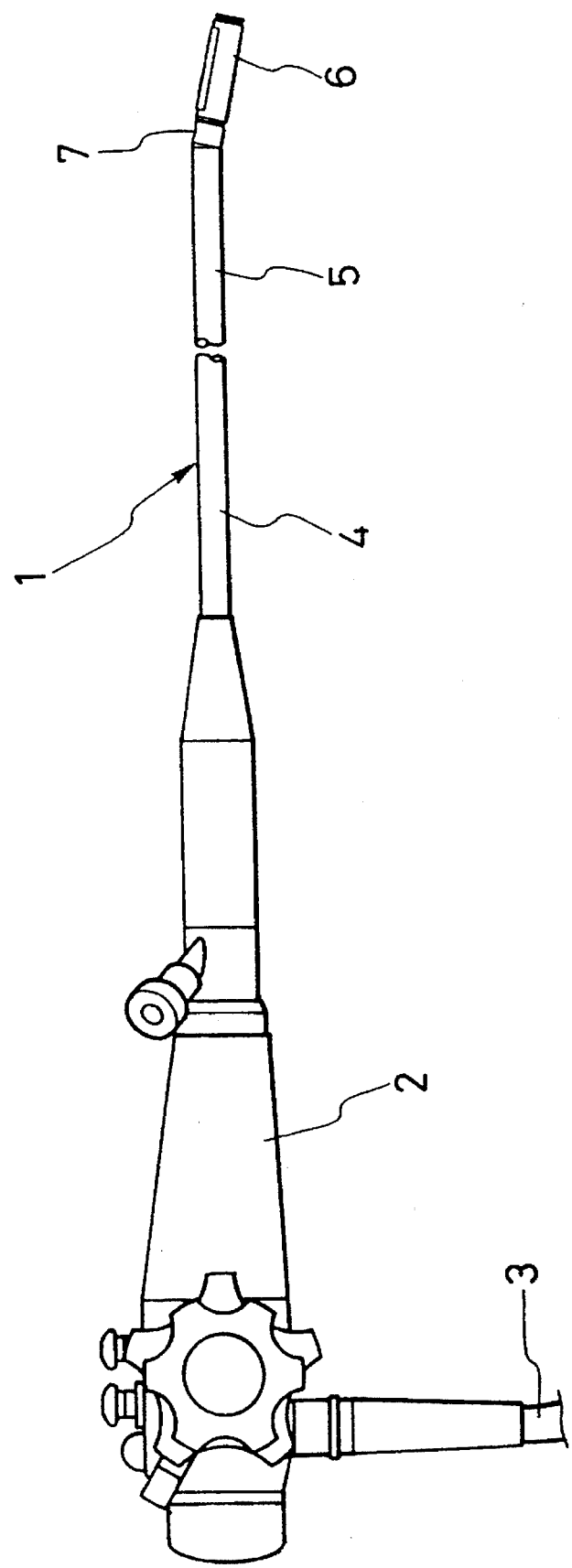
FIG. 1 is a schematic illustration showing the general arrangement of a catheter type endoscopic ultrasound probe embodying the present invention.

Hereafter, the invention is described more particularly by way of a preferred embodiment shown in the drawings. In the particular embodiment shown, the catheter type ultrasound probe of the invention is arranged as an endoscopic ultrasound probe, but it is to be understood that the ultrasound probe is not necessarily required to include endoscopic observation means.

Figure 2:
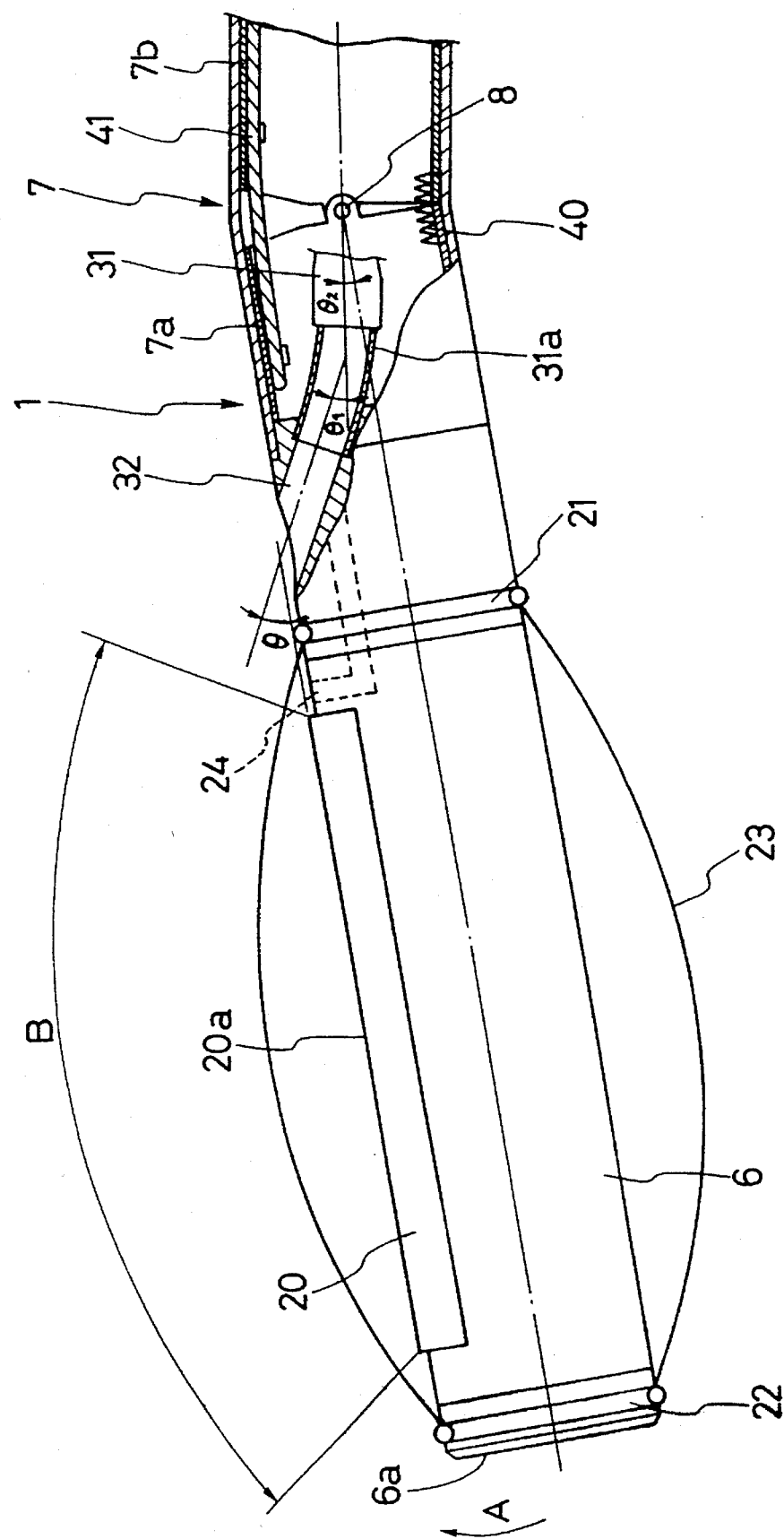
FIG. 2 is a partly sectioned outer view of a rigid fore end section of a catheter member of the probe.

Referring to FIGS. 1 and 2, the endoscopic ultrasound probe according to the invention includes a catheter member 1, a main body 2 with manipulating control means, and a universal cable 3. The catheter member 1 is constituted by a flexible body section 4 (hereinafter referred to as "a flexible section" for brevity) which can bend itself along an intracavitary path of insertion, except its proximal end which is connected to the operating unit, an angle section 5 which is connected to the fore end of the flexible section 4, and a rigid fore end section 6 which is connected to the fore end of the angle section 5. The angle section 5 and the rigid fore end section 6 are connected with each other through an articular joint section 7. As shown particularly in FIG. 3, the articular joint section 7 is constituted by a front joint pipe 7a, which is fixedly connected to the rigid fore end section 6, and a rear joint pipe 7b, which is fixedly connected to the angle section 5, the front and rear joint pipes 7a and 7b being pivotally connected with each other at opposite lateral side portions by pins 8. Consequently, along with the front joint pipe 7a, the rigid fore end section 6 at the tip end of the catheter member 1 can be turned about the pins 8 of the articular Joint section 7 to take an angularly bent position within a predetermined range as indicated by arrow A in FIG. 2.

Figure 4:
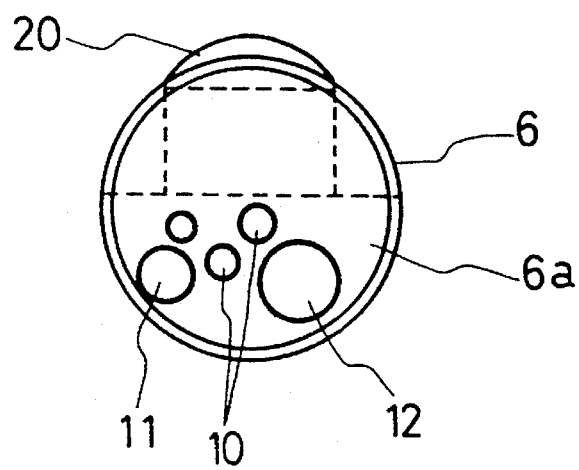
FIG. 4 is a schematic end view of the rigid fore end section of the catheter member.

As shown in FIG. 4, the rigid fore end section 6 is provided with endoscopic observation means on its distal end face 6a, including an illumination window 10 and an observation window 11. A light emitting end of an illumination light guide is disposed in the illumination window 10, while an objective lens is fitted in the observation window to form optical images of a subject on a predetermined plane where a solid-state image sensor element is located thereby to convert endoscopic optical images into electric signals. Further, an biopsy channel 12 is opened on the distal end face 6a to protrude forceps or other instrument therefrom. The arrangements of these endoscopic observation and biopsy channel 12 are known, so that further description and illustration in this regard are omitted for the sake of simplicity of explanation.

An ultrasound transducer 20 is mounted on the rigid fore end section 6 at a position closer to its proximal end away from the distal end with the above-described endoscopic observation means. The ultrasound transducer 20 is constituted by a large number of traducer elements which are arrayed in a row in the axial direction of the rigid fore end section 6 for electronic convex or linear scanning operations with a view field as indicated by arrows B in FIG. 2 for ultrasound image observation. On the front and rear sides of the ultrasound transducer 20, the rigid fore end section 6 is provided with annular grooves 21 and 22 which serve to anchor fixedly therein the opposite ends of a tubular balloon 23 by the use of rubber rings or other suitable fixation means. A nozzle 24 which supplies an ultrasound transmissive medium like deaerated water to and from the balloon 23 is opened on the girder of the rigid fore end section 6 at an intermediate position between the ultrasound transducer 20 and the annular groove 22. Namely, the balloon which is fitted on the rigid fore end section 6 is inflated with the ultrasound transmissive medium which is supplied through the nozzle 24.

Figure 5:
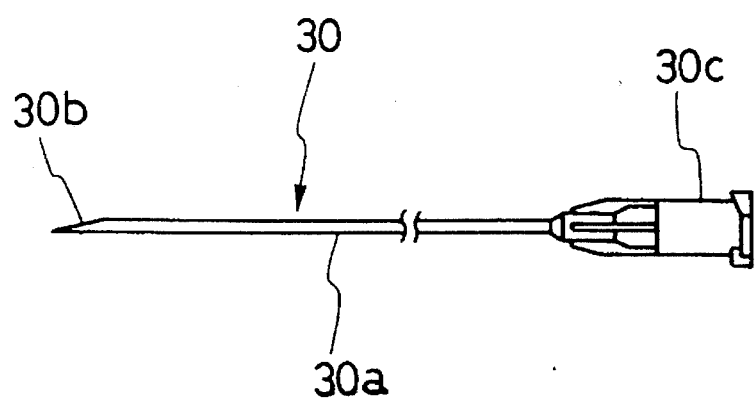
FIG. 5 is a schematic illustration of a typical puncture needle construction.

Indicated at 30 is a puncture needle which has a hollow needle body 30a with a sharp-pointed end 30b as shown in FIG. 5. Through a needle entrance 7 which is provided on the main body 2, the puncture needle 30 is introduced into a needle guide passage 31 which extends as far as the rigid fore end section 6 through the main body 2 and the flexible and angle sections 4 and 5 of the catheter member 1 to project the puncture needle 30 through an exit 32 which is opened on a lateral side of the rigid fore end section 6. The proximal or base end of the puncture needle 30 is terminated with a coupler 30c of an increased diameter which is connectible to a injection medicine supply means or to a drainage means.

In the flexible section 4 and the angle section 5, the puncture needle guide passage 31 is constituted by a flexible tube which runs axially through the catheter member 1. However, since the exit opening 32 for the puncture needle 30 is provided on a lateral side of the rigid fore end section 6, it is necessary to turn the axial needle passage 31 smoothly toward the exit opening 32 through the articular joint section 7 and part of the rigid fore end section 6. For this purpose, the fore end of the flexible tube of the axial needle passage 31 is connected to the needle exit opening 32 through a curved needle passage 31a in the form of a hard rigid pipe with a predetermined turn angle toward the exit opening 32. Namely, the linear needle guide passage 31 is connected to the curved needle passage 31a within the front joint pipe member 7a of the articular joint section 7 to turn the passage for the puncture needle 30 through a predetermined angle $\theta_1$ with the axis of the catheter member 1. As the rigid fore end section 6 is bent through an angle $\theta_2$ at the articular joint section 7, the puncture needle 30 is projected out of the needle passage at an angle of $\theta=\theta_1+\theta_2$ relative to the active surface 20a of the ultrasound transducer 20 on the rigid fore end section 6.

Figure 3:
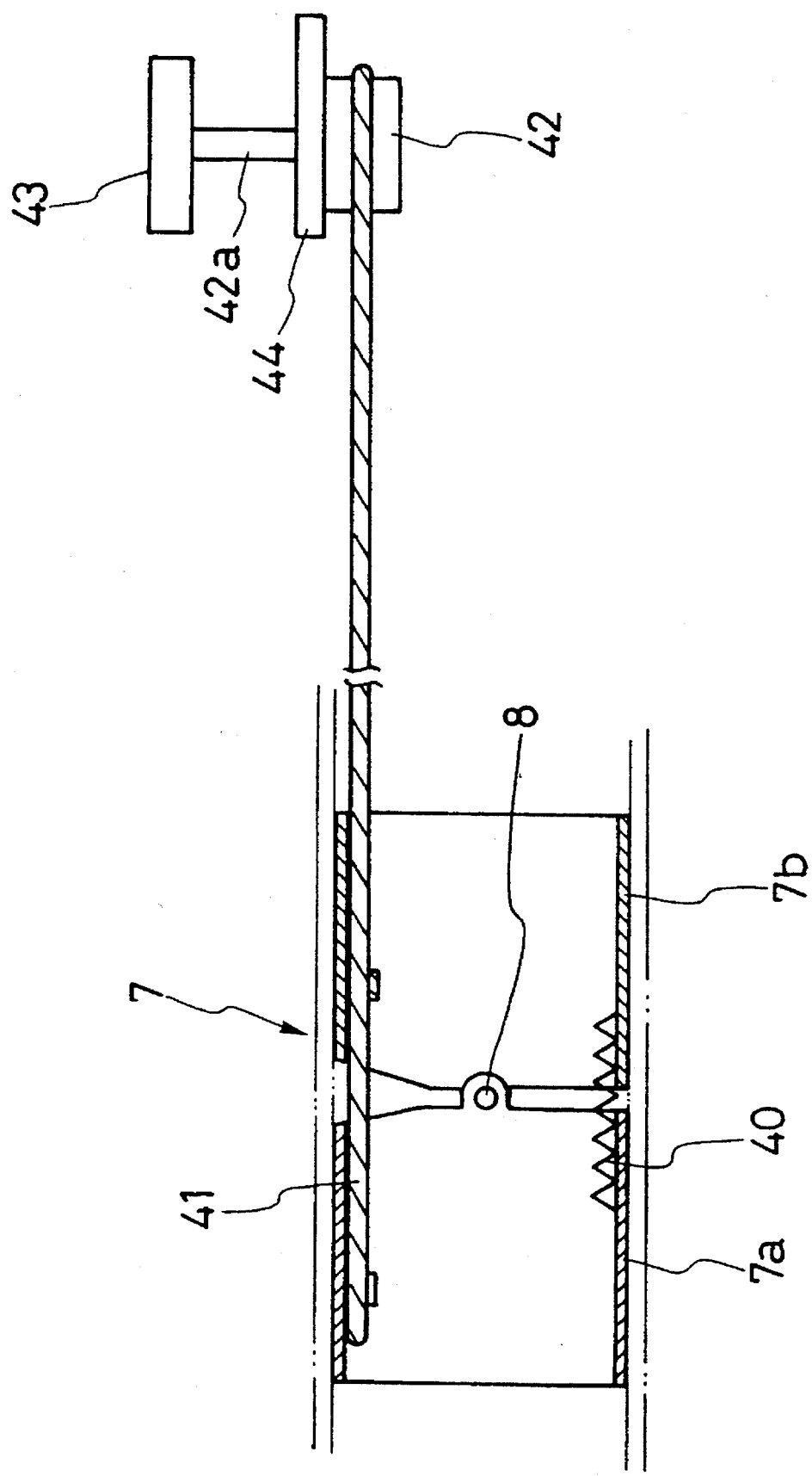
FIG. 3 is a fragmentary sectional view of an articular joint section of the catheter member.

As mentioned hereinbefore, the angle of the rigid fore end section 6 relative to the axis of the catheter member 1 is adjustable through the articular joint section 7 which is pivotable to bend the rigid fore end section 6 in a direction rearward of the active surface of the ultrasound transducer 20 on a lateral side of the rigid fore end section 6. Normally, the rigid fore end section 6 is urged into a bent position of a predetermined angle by a spring 40 which is tensioned between the front and rear pipe members 7a and 7b of the articular joint-section 7. On the other hand, as shown in FIG. 3, a joint operating wire 41 which is extended from the operating section 2 through the catheter member 1 is fixedly connected at its fore end to an inner surface of the front pipe 7a of the articular joint section 7 at a radially opposite position or with a 180° phase difference relative to the biasing spring 40. The proximal end portion of the joint operating wire 40 is wound on a spool 42 which is rotatably mounted within the main body 2 of the probe. The spool 42 has its rotational shaft 42a extended out of the casing of the main body 2 and fitted with a knob 43 at its outer end, so that the joint operating wire 41 can be pulled back and forth by turning the knob 43. When the joint operating wire 41 is pulled backward or toward the main body 2, the rigid fore end section 6 is turned toward its straight axial position against the biasing force of the spring 40. The spool 42 is releasably engaged with a lock member 44 which blocks rotational movements of the spool 42 to retain the joint operating wire 41 in a desired pulled state. Namely, the rigid fore end section 6 can be set in a desired angular position relative to the axis of the catheter member 1 by applying the lock member 44.

With the above-described arrangements according to the present invention, for example, the catheter member 1 can be introduced into the stomach through the throat and esophagus for intragastric examination by the endoscopic means or for ultrasound tomographic examination by the ultrasound transducer 20. If necessary, the puncture needle 30 can be driven out of the needle passage to penetrate into the pancreas or other organs through the gastric wall for injection of medicine or contrast medium or for drainage.

On insertion of the endoscopic ultrasound probe into the digestive tract, the catheter member 1 has to be passed through the throat where the path of insertion turns at a large angle to make the passage of the catheter member 1 extremely difficult especially when it has a lengthy rigid fore end section to accommodate endoscopic observation means in addition to the electronic scan type ultrasound transducer 20. Needless to say, if in a straight form, such a lengthy rigid fore end section will give considerable pains to the patient upon passage through the throat. However, according to the invention, the rigid fore end section 6 is normally bent by a predetermined angle $\theta$ off the axis of the catheter member 1 at the articular joint section 7, so that it can be smoothly passed around an angular bend in the path of insertion as at the throat by orienting the bent fore end section to lie in the same direction as the bend in the path of insertion, lessening the pains on the part of the patient. Past the throat portion, the catheter member 1 is introduced into the esophagus which is substantially in the form of a straight tube. Therefore, this time the front pipe member 7a of the articular joint section 7 can be turned into a straight position relative to the rear pipe 7b by pulling the wire 41 toward the main body 2, permitting the catheter member 1 to advance smoothly through the esophagus and then into a gastric or other region to be examined. Nevertheless, since the esophagus is a canal of a flattened or elliptic shape in section, the rigid fore end section even in the bent position can be passed smoothly therethrough as long as the flat sides of the bent fore end section are kept in the direction of the longer side of the elliptic canal.

In order to carry out an ultrasonic examination within the stomach, the balloon 23 is filled and inflated with an ultrasound transmissive medium, and the ultrasound transducer 20 is faced toward a gastric wall of interest. However, in some gastric wall regions, it is difficult for the catheter member to transmit and receive ultrasound signals exactly in a perpendicular direction due to limitations connected with the direction of insertion of the catheter member 1 and the direction of signal transmission and reception by the ultrasound transducer. Generally, more often than not the ultrasound transducer 20 on the rigid fore end section 6 can be properly faced toward an aimed intracavitary wall portion when the rigid fore end section is bent off the axis of the catheter member 1 in a direction rearward of the active surface of the ultrasound transducer. Therefore, the rigid fore end section 6 of the catheter member 1 is normally retained in a bent position by the action of the spring 40 which is provided on the articular joint section 7. In this connection, if the ultrasound transducer 20 on the rigid fore end section 6 is fixed in a particular direction, a difficulty may be experienced in turning the transducer into an optimum direction for signal transmission and reception by an angling operation of the angle section 5. However, on such an occasion, the ultrasound transducer 20 can be more easily turned into a desired direction simply by pulling the wire 41 forward or backward. This permits to adjust the ultrasound transducer into an optimum direction for signal transmission and reception without moving the catheter member 1 as a whole.

When the puncture needle 30 is driven to penetrate the pancreas or other target organ through an intracavitary wall, the puncturing operation is monitored by way of the ultrasound images produced by the transducer 30. At this time, the puncture needle 30 is driven forward through the axial needle passage 31 and the curved passage 31a and projected through the exit opening 31a to penetrate the needle point 30b into a target portion through an intracavitary wall. In this regard, in order to let the needle point 30b reach a target depth smoothly, it is desirable to transmit the driving thrust force to the needle point 30a effectively to a sufficient degree. For this purpose, the hollow body 30a of the puncture needle 30 should preferably be of high rigidity material although it has to be launched from the needle passage 31 turning toward the exit opening 32 on a lateral side of the rigid fore end section 6 through the curved needle passage 31a. In this connection, the rigid fore end section 6 can be set in a bent position at the angle of $\theta_2$ at maximum with respect to the axis of the catheter member 1 by flexing the articular joint section 7, so that, even though the angle of the curved needle passage 31a relative to the axis of the catheter member 1 is as shallow as $\theta_1$, the puncture needle 30 can be launched at the angle of $\theta_1+\theta_2=\theta$ relative to the active face of the ultrasound transducer 20. Accordingly, this reduction of the turn angle of the curved needle passage makes it possible to drive the puncture needle 30 toward the exit 32 of the needle passage 31 more easily, enhancing the needle drivability and operationability in puncturing operations. For instance, in case one needs to project the puncture needle 30 at an angle of 30° with the ultrasound transducer 20, the turn angle of the curved needle passage 31a can be reduced to 20° by setting the rigid fore end section 2 in a bent position 10° off the axis of the catheter member by way of the articular joint section 7. It follows that the puncture needle 30 with a needle body 30a of higher rigidity can be smoothly passed through the curved passage 31a, and therefore a propelling force can be effectively applied to the needle body 30a to get the needle point 30b to a target.

In the foregoing embodiment, the present invention has been described by way of an ultrasound probe for examination of the upper digestive system including the stomach and a puncturing operation into the pancreas. However, needless to say, the invention is not restricted to the particular examples shown. Further, there are no restrictions in particular with regard to the projection angle of the puncture needle relative to the ultrasound transducer and the turn angle of the curved needle passage section from the axial needle passage.

As clear from the foregoing particular description, the ultrasound probe according to the invention has the articular joint section connected to the proximal end of the rigid fore end section of the catheter member to hold the latter normally held in a bent position at a predetermined angle with the axis of the catheter member in a direction rearward of the active surface of the ultrasound transducer on the rigid fore end section. The angle of the rigid fore end section in the position can be varied within a predetermined range by pulling the wire back and forth. Therefore, even if the intracavitary path of insertion contains a bend or bends of a relatively large angle, the catheter member can be inserted smoothly around the bend by orienting the bent fore end section to lie in the same direction as the bend in the path of insertion. Further, for transmission and reception of ultrasound signals, the active face of the ultrasound transducer can be easily turned into a desired direction at the time of fine adjustment of the direction of signal transmission and reception. Moreover, in projecting a puncture needle at a given angle through a curved passage which connects the axial needle passage to an exit opening on a lateral side Of the rigid fore end section of the catheter member, the turn angle of the curved needle passage can be minimized to such a degree as to make it possible to pass therethrough a hard puncture needle of higher rigidity to ensure higher needle operationability and drivability.

What is claimed is:

1. A catheter type ultrasound probe having an ultrasound transducer mounted on a rigid fore end section at the tip end of a soft and flexible body section of a catheter member to be introduced into an intracavitary portion, characterized in that the catheter member comprises:

an articular joint section connected between said rigid fore end section and said flexible body section, said articular joint section having front and rear joint members pivotally connected with each other for angular flexing movements in directions forward and rearward of an active face of said ultrasound transducer on said rigid fore end section;

a biasing means mounted on said articular joint section and adapted to urge said front joint member constantly rearward of said active face of said ultrasound transducer into a bent position off the axis of said body section of said catheter member along with said rigid fore end section; and a joint operating wire means connected to said joint member to turn same back into a straight axial position against the biasing action of said biasing means.

2. A catheter type ultrasound probe as defined in claim 1, wherein said articular joint section is constituted by a couple of pivotally connected rigid rings including a front ring fixedly connected to said rigid fore end section of said catheter member, and said joint operating wire means is connected to said front ring of said articular joint section.

3. A catheter type ultrasound probe as defined in claim 1, further comprising a puncture needle guide passage extending axially through said flexible body section and turning toward an exit opening on a lateral side of said rigid fore end section through a curved passage section provided on said front ring of said articular joint section and part of said rigid fore end section of said catheter member.

4. A catheter type ultrasound probe as defined in any of claims 1 to 3, further comprising endoscopic observation means accommodated on said rigid fore end section of said catheter member in addition to said ultrasound transducer.

\* \* \* \* \*